US011033226B2

(12) United States Patent
Guidotti et al.

(10) Patent No.: US 11,033,226 B2
(45) Date of Patent: Jun. 15, 2021

(54) DETECTING NON-EVIDENT CONTRIBUTING VALUES

(71) Applicant: International Business Machines Corporation, Armonk, NY (US)

(72) Inventors: Alice Guidotti, Rome (IT); Elia Tufarolo, Rome (IT); Agostino Sturaro, Cona (IT); Leonardo Rosati, Rome (IT)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/580,135

(22) Filed: Sep. 24, 2019

(65) Prior Publication Data
US 2021/0085239 A1    Mar. 25, 2021

(51) Int. Cl.
| | |
|---|---|
| *A61B 5/00* | (2006.01) |
| *G06N 5/02* | (2006.01) |
| *G06N 5/04* | (2006.01) |
| *G08B 6/00* | (2006.01) |
| *G08B 21/02* | (2006.01) |
| *A61B 5/16* | (2006.01) |

(52) U.S. Cl.
CPC .............. *A61B 5/486* (2013.01); *A61B 5/165* (2013.01); *A61B 5/7275* (2013.01); *A61B 5/746* (2013.01); *G06N 5/02* (2013.01); *G06N 5/04* (2013.01); *G08B 6/00* (2013.01); *G08B 21/0211* (2013.01)

(58) Field of Classification Search
CPC ......... A61B 5/486; A61B 5/746; A61B 5/165; A61B 5/7275; G06N 5/02; G06N 5/04; G08B 6/00; G08B 21/0211
USPC ....................................................... 340/573.1
See application file for complete search history.

(56) References Cited

U.S. PATENT DOCUMENTS

| | | | |
|---|---|---|---|
| 6,497,577 B2 | 12/2002 | Kanter | |
| 10,748,644 B2* | 8/2020 | Shriberg | ................ G16H 15/00 |
| 2011/0118558 A1* | 5/2011 | Barr | ........................ A61B 5/16 600/300 |
| 2012/0289788 A1 | 11/2012 | Jain et al. | |
| 2012/0289789 A1 | 11/2012 | Jain et al. | |
| 2012/0290215 A1 | 11/2012 | Adler et al. | |
| 2015/0237834 A1* | 8/2015 | Schab | .................... A61B 5/112 340/573.3 |
| 2016/0063874 A1* | 3/2016 | Czerwinski | .......... G06Q 10/107 434/236 |

(Continued)

OTHER PUBLICATIONS

Mozos et al., "Stress Detection Using Wearable Physiological and Sociometric Sensors", International Journal of Neural Systems, vol. 0, No. 0 (9999) 1-17, <http://www.detcp.upct.es/Personal/OMartinez/publications/mozos2016ijns.pdf>.

(Continued)

*Primary Examiner* — Hirdepal Singh
(74) *Attorney, Agent, or Firm* — Aaron N. Pontikos

(57) ABSTRACT

A tool for distress management. The tool determines a level of distress associated with a user. The tool identifies a next action to be performed by the user. The tool determines a level of distress associated with the next action. The tool determines whether the associated level of distress exceeds a predetermined threshold. Responsive to a determination that the associated level of distress exceeds the predetermined threshold, the tool alerts the user of an impact to the level of distress associated with the user.

20 Claims, 4 Drawing Sheets

(56) References Cited

U.S. PATENT DOCUMENTS

| | | | | |
|---|---|---|---|---|
| 2016/0302711 | A1* | 10/2016 | Frank | A61B 5/746 |
| 2016/0335405 | A1* | 11/2016 | Perunov | G06F 19/00 |
| 2017/0072162 | A1* | 3/2017 | Kim | A61M 21/02 |
| 2018/0000414 | A1 | 1/2018 | Lowet et al. | |
| 2018/0132776 | A1* | 5/2018 | Flickinger | A61B 5/6898 |
| 2018/0184901 | A1 | 7/2018 | Akmandor et al. | |
| 2018/0301224 | A1 | 10/2018 | Matichuk et al. | |
| 2018/0310867 | A1 | 11/2018 | Sivan et al. | |
| 2019/0091403 | A1* | 3/2019 | Osorio | G16H 20/17 |
| 2019/0164406 | A1* | 5/2019 | Werner | H04L 51/32 |
| 2019/0167209 | A1* | 6/2019 | Annoni | A61B 5/0816 |
| 2020/0037964 | A1* | 2/2020 | Gujral | A61B 5/165 |

OTHER PUBLICATIONS

Statista, "Number of data centers worldwide in 2015, 2017, and 2021 (in millions)", by Statista Research Department, last edited Feb. 25, 2019, 2 pages, <https://www.statista.com/statistics/500458/worldwide-datacenter-and-it-sites/>.

Statista, "Size of the multi-tenant data center market by segment worldwide from 2013 to 2021 (in million U.S. dollars)", by Statista Research Department, last edited Aug. 27, 2018, 2 pages, <https://www.statista.com/statistics/901453/multi-tenant-data-center-market-by-segment-worldwide/>.

Stewart, James A., "The Detrimental Effects of Allostasis: Allostatic Load as a Measure of Cumulative Stress", Journal of Physiological Anthropology, vol. 25, 2006, Accepted: Oct. 18, 2005, pp. 133-145.

* cited by examiner

DETECTING NON-EVIDENT CONTRIBUTING VALUES

BACKGROUND OF THE INVENTION

The present invention relates generally to cognitive computing systems, and more particularly to machine learning for detecting non-evident contributing values.

The existence of cumulative distress is well documented. Cumulative distress is caused by compounding past events, which may be considered simple events when examined alone. Additionally, cumulative distress can be measured as a whole at a certain point in time. Furthermore, existing sensors can measure cumulative distress in real-time.

SUMMARY

Aspects of an embodiment of the present invention disclose a method, a computer system and a computer program product for distress management. The method includes determining, by one or more computer processors, a level of distress associated with a user. The method includes identifying, by the one or more computer processors, a next action to be performed by the user. The method includes determining, by the one or more computer processors, a level of distress associated with the next action. The method includes determining, by the one or more computer processors, whether the associated level of distress exceeds a predetermined threshold. Responsive to a determination that the associated level of distress exceeds the predetermined threshold, the method includes alerting, by the one or more computer processors, the user of an impact to the level of distress associated with the user.

DETAILED DESCRIPTION

Figure 1:
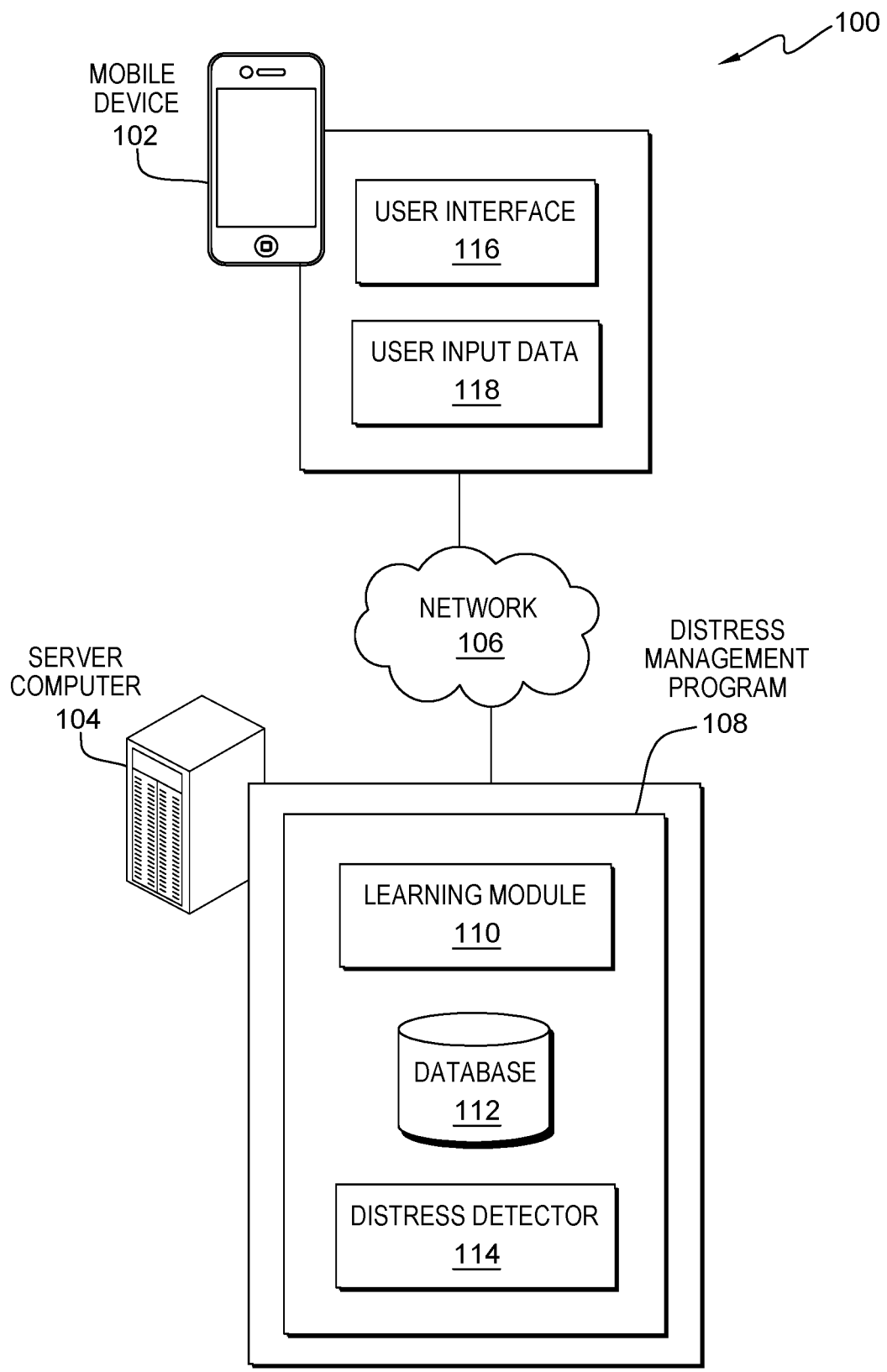
FIG. 1 is a functional block diagram illustrating a data processing environment suitable for operation of a distress management program, in accordance with an embodiment of the present invention.

Embodiments of the present invention recognize that identifying sources of distress for an individual may reduce the risk of developing potential health issues. Embodiments of the present invention further recognize that existing sensors can measure distress levels, but do not automatically correlate those measurements with the events being performed by a user. Embodiments of the present invention further recognize that uncovering sources of distress when those sources are not immediately evident can be beneficial to an individual susceptible to developing potential health issues. Embodiments of the present invention recognize that every individual has a varying level of distress that can be considered critical, and the analysis of the root causes needs to take into account the specific reactions of each individual. Embodiments of the present invention recognize that the function of cumulative distress is complex, the identification of historical events for an individual is paramount in avoiding elevated levels of distress. Embodiments of the present invention recognize that, while distress, as a general concept, might be well defined, this concept lacks any kind of recognized computer representation.

Embodiments of the present invention provide a recognizable computer representation of distress for a user, where the computer representation detects non-evident factors contributing to a level of distress of the user and distills those factors into workable numerical values that can be measured and scaled to predict an impact to the level of distress of the user. For purposes of this disclosure, a level of distress is a cumulative numerical value representing a plurality of contributing values (e.g., physiological data for a user, event/action data for a user, user input data, etc.) impacting perceived distress for a user. A critical level of distress for a user is a threshold value indicating that an undesirable level of distress has been reached.

Embodiments of the present invention provide the capability to detect discrete sources of distress once a critical level of distress has been reached for an individual. Embodiments of the present invention provide the capability to train a solution utilizing identified historical sources of distress that will inform an individual of a possibility to reach a critical level of distress. Embodiments of the present invention provide the capability to recommend certain actions to avoid in order to lessen a risk of reaching a critical level of distress. Embodiments of the present invention provide a cognitive system that determines various negative events that cumulatively bear responsibility of elevating a level of distress for an individual. Embodiments of the present invention provide the capability to alert an individual of a sequence of negative events that previously elevated a level of distress to a critical level and provide recommendations for breaking and avoiding the sequence of events that cumulatively contributed to elevating the level of distress to a critical level.

The inventor has further observed and/or recognized that sources of distress in an individual might not be evident in cases where distress is generated by a combination of external factors spread out across various events over time, some of which remain distant in time from noticeable peaks in a level of distress. Moreover, distress may not be evident where positive events mitigate distress factors occurring between external events that generate distress, thereby hiding distressful events for purposes of diagnosis.

The inventor has further observed and/or recognized that when reaching a critical level of distress, it may be difficult to clearly remember each event that cumulatively led to the critical level of distress, and to further objectively weight each event to identify relevant factors while excluding circumstantial and irrelevant details. Moreover, upon reaching a critical level of distress, a common human reaction is to focus on an immediate cause of the distress (e.g., a most recent distressful event), which might represent a relatively small part of an accumulating distress level.

The inventor has further observed and/or recognized that certain events can have varying effects on a level of distress depending on different preceding events. For example, where "driving" is the certain event, driving after not having enough sleep may increase distress levels, and conversely, driving home after leaving work may reduce distress levels. In another example, where "running" is the certain event, running for exercise may reduce distress levels, and conversely, running after missing a bus may increase distress levels. The inventor has further observed that capturing this knowledge, and training a machine learning model on different sequences of events, paired with a level of distress measured at the end of the sequence of events, provides a system that learns to recognize patterns in the sequences of events that increase levels of distress or reduce levels of distress. A learned rule provides the capability to evaluate future sequences of events that are similar to historical sequences of events, and form educated predictions as to what events a user should avoid in order to reduce a total cumulative level of distress.

Implementation of such embodiments may take a variety of forms, and exemplary implementation details are discussed subsequently with reference to the Figures.

Referring now to various embodiments of the invention in more detail, FIG. 1 is a functional block diagram of a distributed data processing environment, generally designated 100, suitable for operation of a distress detector program in accordance with at least one embodiment of the invention. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes mobile device 102 and server computer 104, interconnected over network 106. Network 106 can be, for example, a telecommunications network, a local area network (LAN), a wide area network (WAN), such as the Internet, or a combination of the three, and can include wired, wireless, or fiber optic connections. Network 106 may include one or more wired and/or wireless networks that are capable of receiving and transmitting data, voice, and/or video signals, including multimedia signals that include voice, data, and video information. In general, network 106 may be any combination of connections and protocols that will support communications between mobile device 102 and server computer 104, as well as other computing devices (not shown) within distributed data processing environment 100. FIG. 1 is intended as an example and not as an architectural limitation for the different embodiments.

In one embodiment, mobile device 102 may be a laptop computer, tablet computer, smartphone, smartwatch, or any programmable electronic device capable of communicating with various components and devices within distributed data processing environment 100, via network 106. In general, mobile device 102 may represent any programmable electronic device or combination of programmable electronic devices capable of executing machine readable program instructions and communicating with other computing devices (not shown) within distributed data processing environment 100 via a network, such as network 106. More specifically, mobile device 102 represents any device capable of monitoring data and receiving user input. In another embodiment, mobile device 102 may represent a sensor, or a collection of connected sensors (i.e., paired smart watch, heart monitor and any other wearable electronic device, etc.), capable of collecting input data related to physical conditions of a user. Mobile device 102 includes user interface 116 and user input data 118.

In one embodiment, user interface 116 provides an interface between a user of mobile device 102 and server computer 104. In one embodiment, user interface 116 may be a graphical user interface (GUI) or a web user interface (WUI) and can display text, documents, web browser windows, user options, application interfaces, and instructions for operation, and include the information (such as graphic, text, and sound) that a program presents to a user and the control sequences the user employs to control the program. In another embodiment, user interface 116 may also be mobile application software that provides an interface between a user of mobile device 102 and server computer 104. Mobile application software, or an "app," is a computer program that runs on smartphones, tablet computers, smartwatches and any other mobile devices.

In one embodiment, user input data 118 may be user input data regarding physiological data of a user. For example, user input data 118 may include user input data gathered from a wearable electronic device, such as mobile device 102, or any other sensors capable of collecting input data related to physiological data of the user, such as heart rate, blood pressure, pupillary dilation, oxygen levels, body temperature, respiratory rate, etc. In another example, user input data 118 may include user input data extrapolated from sentiment analysis of communications (e.g., phone calls, electronic mail and text, etc.) collected from a mobile device, such as mobile device 102. In other embodiments, user input data 118 may include user input related to occurring situations and actions from a plurality of sources, such as communications metadata, structured or semi-structured data, unstructured data and general user input collected from a mobile device, such as mobile device 102. For example, user input data 118 may include communications metadata such as call logs, saved electronic mail, contacts and senders, etc. In another example, user input data 118 may include structured data, such as geolocation, weather, social media posts, calendar entries and applications, as well as unstructured data, such as noise and actions. In an embodiment of the present invention, user input data 118 may be combined in a list of events, where each event in the list of events is defined as follows: [action, date, hour, duration, position, total distress value].

In one embodiment, server computer 104 can be a stand-alone computing device, a management server, a web server, a mobile computing device, or any other electronic device or computing system capable of receiving, sending, and processing data. In other embodiments, server computer 104 can represent a server computing system utilizing multiple computers as a server system, such as in a cloud computing environment. In an embodiment, server computer 104 represents a computing system utilizing clustered computers and components (e.g., database server computers, application server computers, etc.) that act as a single pool of seamless resources when accessed within distributed data processing environment 100. Server computer 104 includes distress management program 108 communicatively coupled to server computer 104. Server computer 104 may include internal and external hardware components, as depicted and described in further detail with respect to FIG. 4.

In one embodiment, distress management program 108 operates on a central server, such as server computer 104 and may be utilized by one or more mobile devices, such as mobile device 102, via network 106. In another embodiment, distress management program 108 may be a program downloaded from the central server or a third-party provider (not shown), and executed on a mobile device, such as mobile device 102, to detect discrete sets of individual causes of distress and train a solution that will alert a user of a potential to reach a critical level of distress. In another embodiment, distress management program 108 may be a program, downloaded from a central server, such as server computer 104 and installed on one or more mobile devices, such as mobile device 102. In yet another embodiment, distress management program 108 may be utilized as a software service provided by a third-party cloud service provider (not shown). In yet another embodiment, distress management program 108 may include one or more components, such as add-ons, plug-ins, and agent programs, etc., installed on one or more mobile devices, such as mobile device 102, to determine a series of events responsible for elevating user distress to a critical level of distress, and through machine learning methods, preemptively alerting a user of a potential for reoccurrence of a similar series of events in order to prevent future escalation to the critical level of distress.

In one embodiment, distress management program 108 is a program for providing the capability to determine a sequence of events that cumulatively contribute to elevating a level of distress to a critical level for a user, and, based on user input, train a solution that will alert the user of sequences of events to avoid to mitigate escalation of the level of distress to the critical level. In one embodiment, distress management program 108 provides a cognitive system that determines each event responsible for a rise in distress for a user, and through leveraging machine learning, provides a mechanism for avoiding similar future events to prevent cumulative critical distress. In one embodiment, distress management program 108 provides the capability to forecast future events that may lead to a critical level of distress by monitoring a plurality of sensors in real-time to determine an impact of discrete events on a level of distress for a user. In one embodiment, distress management program 108 provides post analysis of relevant discrete events and sequences of events once a critical level of distress is reached to learn and develop a knowledge base for potential future events that contribute negatively to a level of distress for a user. In one embodiment, distress management program 108 provides a mechanism for identifying combinations of factors and sequences of discrete events in a particular order that may impact a level of distress for a user. In one embodiment, distress management program 108 provides the capability to identify future relevant causes of cumulative distress for a user and alert the user of a possibility to reach a critical level of distress by applying a learned distress prediction rule to predict a level of distress for a user during observed sequences of events. In one embodiment, distress management program 108 applies a learned distress prediction rule to a number of possible user actions (i.e., event scenarios) that may occur in the near future, and for each user action, utilizes the learned distress prediction rule to predict a level of distress for the user based on each user action or a sequence of user actions. In one embodiment, distress management program 108 dynamically monitors user activities transparently (i.e., without requiring user interaction) to identify synergies between discrete events and successions of events that elevate distress, and preemptively alert a user when user activities being performed in real-time are deemed likely to elevate distress to a critical level based, at least in part, on a learned distress prediction rule applied to potential future situations. In one embodiment, distress management program 108 provides the capability to recommend user activities that historically have contributed to reducing a level of distress for a user. In one embodiment, distress management program 108 stores, processes and learns sequences of events that lead to a critical level of distress for a user by identifying discrete events in the past that contribute to the current level of distress in a user. In one embodiment, distress management program 108 provides the capability to distill a resulting level of distress to one or more discrete events of the past. Distress management program 108 includes learning module 110, database 112 and distress detector 114.

In one embodiment, learning module 110 is a component embedded within distress management program 108 that provides the capability to learn events that correspond to an escalation in a level of distress for a user. In one embodiment, learning module 110 is a machine learning component that collects a history of events and sequences of events that occurred before the level of cumulative distress reached a critical level for a user, and other events that occurred after. In one embodiment, learning module 110 trains a prediction model based on organized historical data that homogenously represents events and sequences of events occurring at different times over a period of time. In one embodiment, learning module 110 may utilize an algorithm based on a sliding windows technique to determine a discrete event, in a time window, caused an increment on an overall total cumulative distress function. In one embodiment, learning module 110 may utilize a variation of the sliding windows technique leveraging event durations to identify an impact to the overall total cumulative distress function caused by a duration of an event. In another embodiment, learning module 110 may utilize sliding the size of the sliding window to resize the window and check whether the different size enhances identification of relevant events corresponding to a level of distress for a user. In yet another embodiment, learning module 110 may utilize two steps focusing on combinations and sequences of events, where a combination step does not take into account a particular order of events, rather marking relevant events and discarding irrelevant events, and a sequences step analyzes a sequence of occurrences of the marked events. In one embodiment, learning module 110 collects a knowledge base related to historical events that have impacted a level of distress for a user, and generates a predictive model that can be used to evaluate current real-time events and a potential impact on the level of distress for the user. In one embodiment, learning module 110 utilizes a sliding windows technique to create labeled examples (i.e., sequences of actions associated to their cumulative impact on the level of distress for a user), which are used to learn a distress prediction rule that outputs a predicted level of distress for a user based on a sequence of events that have occurred, or current actions of the user. For example, given four consecutive events, we can create two examples, each having a sequence of three actions as its features, and the distress level variation as its label. From these four events, event_1=(timestamp_1, distress_level_1, action_1); event_2=(timestamp_2, distress_level_2, action_2); event_3=(timestamp_3, distress_level_3, action_3); event_4=(timestamp_4, distress_level_4, action_4). Where the number "n" of actions in each sequence is set to there, the following two examples are created: example_1={"features"=sequence_of_actions(action_1, action_2, action_3); "label"=(distress_level_3–distress_level_1)}; example_2={"features"=sequence_of_actions(action_2, action_3, action_4); "label"=(distress_level_4–distress_level_2)}.

In one embodiment, database 112 is a storage device (e.g., storage repository, database, etc.) interconnected with a server, such as server computer 104, via a network, such as network 106. In another embodiment, database 112 is logical storage embedded within a program on a server, such as distress management program 108 on server computer 104. In one embodiment, database 112 provides the capability to store data related to user input data, such as user input data 118. For example, database 112 may store data including consented user input data, a user indicated critical level of distress, a user profile and user identification, etc. In another embodiment, database 112 provides the capability to store machine learning data related to a sequence of events that elevate a level of distress for a user. For example, database 112 may store data related to sensor reporting of events, user indicated sequence of events that significantly increased a cumulative distress level, historical sequence of events data and user indicated distress values, etc.

In one embodiment, distress detector 114 is a component embedded within distress management program 108 that provides the capability to alert a user of real-time events that, based on a prediction model and a knowledge base generated by learning module 110, share similarity to historical events and sequences of events that have escalated a level of distress to a critical level for the user. In one embodiment, distress detector 114 provides the capability to evaluate real-time events to determine an impact on a total cumulative distress level for a user. In one embodiment, distress detector 114 provides recommendations to a user of discrete events to avoid mitigating impact on the total cumulative distress level for the user. In another embodiment, distress detector 114 provides recommendations of events determined to reduce cumulative distress, and suggests seeking out these events when a level of distress is reaching a critical level.

Figure 2:
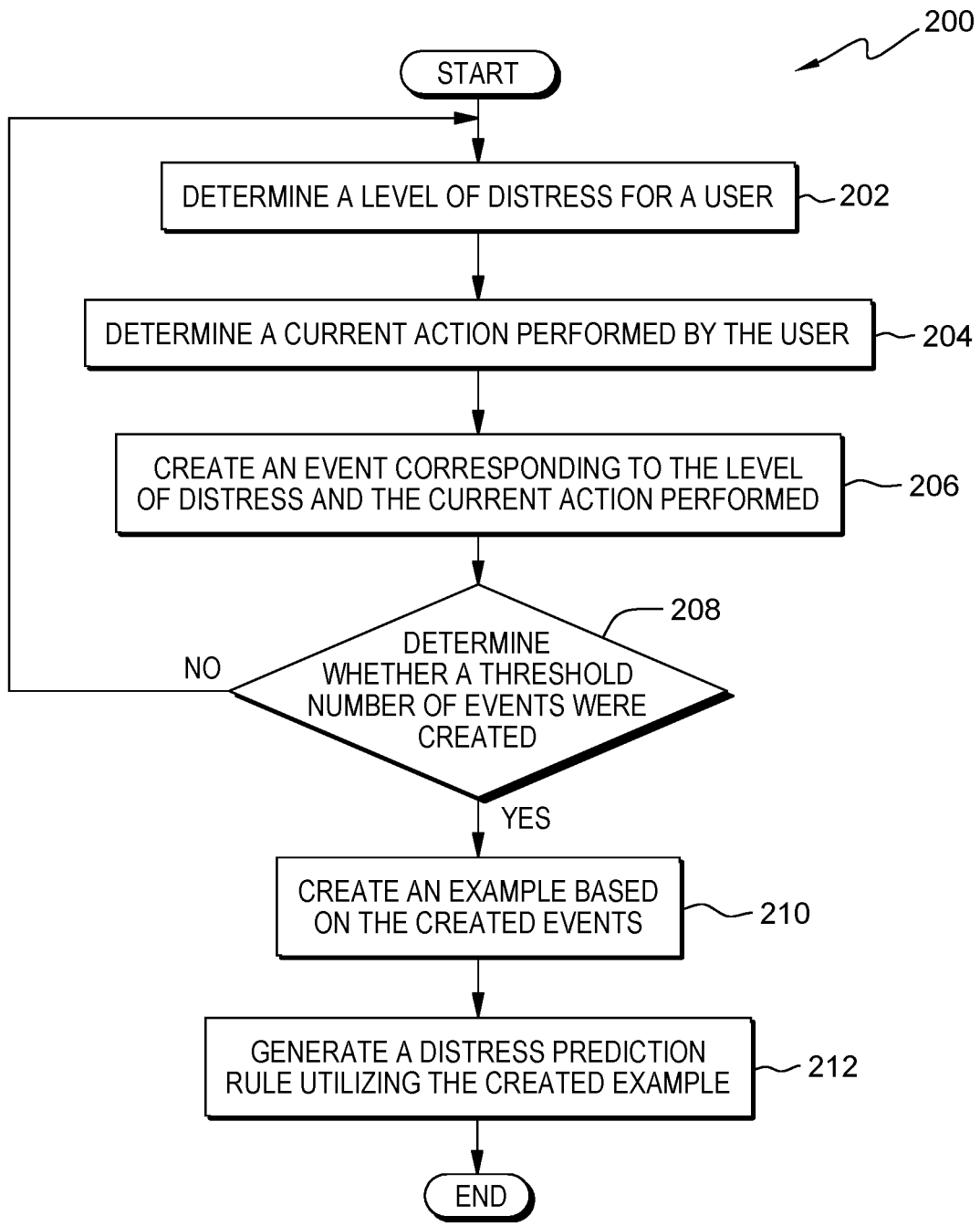
FIG. 2 is a flowchart depicting operational steps of a learning module, in accordance with an embodiment of the present invention.

FIG. 2 depicts a flowchart of operational steps of a distress management program, such as distress management program 108 of FIG. 1, generally designated 200, for performing a learning phase utilizing a learning module, such as learning module 110 of FIG. 1, in accordance with an embodiment of the present invention.

Distress management program 108 determines a level of distress for a user (202). In one embodiment, distress management program 108 determines a level of distress for a user by collecting user input data through one or more sensors. In one embodiment, responsive to a user registering with distress management program 108 and logging in to the system via a mobile device, such as mobile device 102, distress management program 108 collects user input data, such as user input data 118, from the mobile device. In one embodiment, distress management program 108 collects user input data from one or more sensors registered with the user across different points in time (i.e., varying pre-determined time intervals), where the one or more sensors may include the mobile device, such as mobile device 102, and any paired, connected, or linked sensors (e.g., wearable sensors, wearable electronic devices, etc.) associated with the mobile device that are capable of providing sensor values related to physiological quantities associated with the user, communication activities related to the user, location data related to the user and data manually entered by the user. For example, distress management program 108 may collect user input data, such as user input data 118, from a mobile device, such as mobile device 102, and a connected wearable smart watch with the capability to monitor a heart rate of a user. In one embodiment, distress management program 108 collects user input data from various sensors transparently and continuously without requiring a user to manually enter values for a level of distress. For example, distress management program 108 may continuously and transparently monitor a plurality of physiological data, such as heart rate, blood pressure, pupillary dilation, oxygen levels, body temperature, and respiratory rate, etc., during a plurality of events across varying time intervals. In one embodiment, distress management program 108 calculates a level of distress associated with the user based on the user input data collected from one or more sensors. For example, distress management program 108 may identify an elevated heart rate that differs from a previously determined resting heart rate for the user and calculate a level of distress for a user based on the increased heart rate from a paired smart watch with heart monitor capability. In one embodiment, distress management program 108 may determine a total cumulative distress function (e.g., "cumulative_distress(t)") representing a total cumulative distress level for a user based on the user input data collected over a period of time. For example, distress management program 108 may determine a total cumulative distress function by assigning values to a plurality of physiological data and a plurality of event data, scaling the assigned values based on a level of deviation from a predetermined baseline, and combining the assigned values to represent a total cumulative level of distress.

In an alternative embodiment, distress management program 108 determines a critical level of distress for a user by determining whether a critical level of distress is reached from an alert from a user explicitly communicating that the critical level of distress for the user has been reached or exceeded. Upon receiving an alert from a user via a user interface, such as user interface 116 of mobile device 102, indicating that a critical level of distress has been reached or exceeded (e.g., a user has indicated by selecting a button or with a message that their perceived level of distress has exceeded a tolerable level), distress management program 108 determines that a critical level of distress is reached or exceeded. Where a user does not manually log into the system via a user interface to communicate that a critical level of distress has been reached or exceeded, distress management program 108 determines that a critical level of distress is not reached or exceeded. In another embodiment, distress management program 108 determines a critical level of distress is reached where user input data, such as user input data 118, indicates one or more physiological parameters for a user exceeded a predetermined threshold. For example, distress management program 108 may determine a critical level of distress is reached where user input data, such as a respiratory rate value, blood pressure level value, and heart rate value for a user, have exceeded a user indicated acceptable level. In other embodiments, distress management program 108 determines a critical level of distress is reached where a combination of user input data, such as user input data 118, indicates some combination of physiological data, event/action data, sentiment analysis, etc., for a user exceeded a predetermined acceptable threshold. For example, distress management program 108 may determine a critical level of distress is reached where user input data indicates an elevated blood pressure level value in combination with driving home from work exceeds a predetermined acceptable threshold.

Distress management program 108 determines a current action performed by the user (204). In one embodiment, distress management program 108 determines a current action performed by a user by querying the one or more sensors, such as mobile device 102, and associated devices and functionality, for user input data indicative of an action being performed. In one embodiment, the one or more sensors may include a sports application, calendar entries, a global positioning system (GPS) location, call logs, contacts, a duration of a call, sentiment analysis of written communications, voice analysis, weather applications, sleeping applications, a microphone and application usage data, etc. In one embodiment, the current action being performed by the user may include, for example, running or other sports activities, sitting down, answering a phone call, writing an electronic document, meetings, sleeping, and any other conceivable action that may impact a level of distress for a user, etc. In one embodiment, distress management program 108 identifies actions that are currently associated with a user in real-time. For example, distress management program 108 may determine a current action performed by a user by identifying the action as running, based on user input data retrieved from a sports application (e.g., running tracker) and GPS information from a mobile device, such as mobile device 102, and any associated wearable devices and functionalities. In one embodiment, distress management program 108 determines a current action performed by a user by prompting the user to manually indicate the current action. For example, distress management program 108 may prompt the user to enter a current action being performed, and where the user enters "driving", distress management program 108 may determine that the current action performed by the user is driving home from work, based on the user input data entry, the time of day and GPS location information.

In an alternative embodiment, distress management program 108 determines a current action performed by the user by identifying relevant events corresponding to the critical level of distress. In one embodiment, distress management program 108 identifies relevant events corresponding to the critical level of distress by marking a point in time when a user indicated that the critical level of distress was reached or exceeded, and referencing historical events preceding the marked point in time to identify relevant events from the historical events that impacted a value of cumulative distress. In one embodiment, distress management program 108 identifies historical events preceding the marked period in time as relevant events when the historical events correlate to an increase in a value of cumulative distress. In one embodiment, distress management program collects events, sequences of events and a plurality of sensor values for a pre-determined period of time preceding the alert from the user. For example, distress management program 108 marks a point in time, such as Monday, when a user indicated that a critical level of distress was reached, references historical events during a pre-determined period of time preceding the marked point in time, such as Sunday, and further identifies a training exercise on Sunday and a board meeting on Monday as relevant events that significantly increased a value of cumulative distress to the critical level of distress for the user.

Distress management program 108 creates an event corresponding to the level of distress and the current action performed (206). In one embodiment, distress management program 108 creates an event by associating the level of distress and the current action performed, where each event is a data point containing a timestamp that marks the current action performed, a measurement of a level of distress during that action, and a description of the action performed by the user. In one embodiment, an "event" is a single action associated to a measurement of the distress level, differentiating it from an "example", which is a sequence of actions associated with a variation of the distress level. Moreover, some events (and examples) can be associated to a positive decrease of the distress level. In one embodiment, an example may include a set of data points, where the set of data points indicates a sequence of actions performed, a measurement of a level of distress during the sequence of actions, and a description of the sequence of actions performed by the user.

In an alternative embodiment, distress management program 108 creates an event corresponding to the level of distress and the current action performed by associating the critical level of distress to a sequence of events by defining identified relevant events corresponding to the critical level of distress as the sequence of events that escalated a value of cumulative distress to the critical level of distress for a user. In one embodiment, distress management program 108 associates the identified relevant events corresponding to the critical level of distress to a unique user identification (e.g., "user_id"). In one embodiment, distress management program 108 determines whether a user record exists for the user by referencing a knowledge base, such as database 112, and searching for the unique user identification associated with the identified relevant events. Upon determining that the unique user identification is located in the knowledge base, distress management program 108 determines that a user record exists. Upon determining that the unique user identification is not located in the knowledge base, distress management program 108 determines that a user record does not exist for the user identification. Responsive to a determination that a user record does not exist, distress management program 108 creates the user record. In one embodiment, responsive to a first alert by a user that a critical level of distress is reached, distress management program 108 creates a user record and continues to step 208.

Distress management program 108 determines whether a threshold number of events were created (decision block, 208). In one embodiment, distress management program 108 determines whether a threshold number of events were created by comparing a number of created events to a predetermined threshold number of events estimated to return workable results for training a rule to predict distress. Where distress management program 108 determines that the number of created events exceeds the predetermined threshold number of events, distress management program 108 determines that the threshold number of events were created. Where distress management program 108 determines that the number of created events does not exceed the predetermined threshold number of events, distress management program 108 determines that the threshold number of events were not yet created.

Responsive to a determination that the threshold number of events were not yet created (NO branch, 208), distress management program 108 continues to cycle through the preceding steps, beginning with determining a level of distress for a user (202).

Responsive to a determination that the threshold number of events were created (YES branch, 208), distress management program 108 creates an example based on the created events (210). In one embodiment, distress management program 108 creates an example of a sequence of events that correspond to the critical level of distress by aggregating the previous sequence of events in various ways. In one embodiment, distress management program 108 creates an example of a sequence of events associated with a corresponding variation in the level of distress associated with the user, as some examples can show a sequence of events with a decrease in the cumulative level of distress. In one embodiment, distress management program 108 creates an example of a sequence of events as an entry in a user record stored in a database, such as database 112. In one embodiment, distress management program 108 creates an example that represents a new sequence of events that escalated a cumulative level of distress for a user to a critical level of distress. In one embodiment, distress management program 108 creates an example as a first row in a table of the user record, where the first row includes the user identification and the sequence of events that impacted a cumulative level of distress for the user. In one embodiment, distress management program 108 creates an example by processing the set of created events utilizing an algorithm based on a sliding window to generate one or more labeled examples. For example, distress management program 108 may generate a list of created events, such as "event_1=(timestamp_1, distress_level_1, action_1); event_2=(timestamp_2, distress_level_2, action_2); . . . ; event_n=(timestamp_n, distress_level_n, action_n)" where n is the chosen number of time intervals of the same length. Each time interval contains a different event. In one embodiment, distress management program 108 processes the set of created events by applying the algorithm based on the sliding window defined as a function "create_examples(event_1, event_2, . . . , event_n . . . ), which returns the set of labeled examples (210). For example, each example includes a set of features and a label, where the main feature of an example is a sequence of n actions, each being the action of one of n consecutive events, and the label is the variation in a level of distress, calculated by utilizing the measurement of a level of distress at a first action (e.g., event_1) and a last action (e.g., event_n) in the sequence of events. In one embodiment, distress management program 108 processes the set of created events utilizing the function based on the sliding window technique to overlap the sequences of events, creating various new examples. In one embodiment, distress management program 108 stores the created examples in a knowledge base, such as database 112, such that a catalog of examples is collected for providing a training set for a machine learning algorithm to generate a distress prediction rule for predicting potential events or sequences of events that may increment a cumulative level of distress to a critical level of distress, as well as provide recommendations for discrete events to avoid.

In an alternative embodiment, distress management program 108 leverages a sliding window technique to create an example by identifying historical events that increased a value of cumulative distress to the critical level of distress. For example, where shifting the window of one slot (e.g., timing and duration of a historical event) does not decrease the value of cumulative distress, distress management program 108 may determine that the elimination of the historical event is irrelevant to the escalation to the critical level of distress. However, where shifting the window one slot does decrease the value of cumulative distress, distress management program 108 may determine that the elimination of the historical even is relevant to the escalation to the critical level of distress. In another embodiment, distress management program 108 may leverage variations to the sliding window technique, such as event duration, sliding size of the sliding window and combinations and sequences to gather deeper insight into event relevancy, which can reduce noise caused by casual correlations of neutral events that may fall in time between relevant events. For example, distress management program 108 may define shifts by length of a slot (time) and providing different labels to each slot based on a level of cumulative distress at a given point in time. Distress management program 108 may then cross information of different sequences of events to understand whether a sequence of events collectively increase the level of cumulative distress, or whether discrete events have a constant impact (positive, neutral, negative) independent of preceding and subsequent events.

Distress management program 108 generates a distress prediction rule utilizing the created example (212). In one embodiment distress management program 108 generates a distress prediction rule, by training a machine learning subsystem on the new example and on examples generated during previous runs. In one embodiment, distress management program 108 defines the training of the machine learning subsystem as a first function that inputs the list of the created examples and returns a second function that can be applied to subsequent (e.g., hypothetical) events to make distress predictions. In one embodiment, the first function can be a machine learning technique that learns the second function by training on the examples. For example, distress management program 108 may utilize a function "train_and_learn(example_1, example_2, example_n . . . )" that returns a "predict_distress" function. In one embodiment, distress management program 108 applies the "train_and_learn(example_1, example_2, example_n . . . )" function over a predetermined period of time, and with each process, generates a stronger and more accurate "predict_distress" function for a given sequence of created examples. In one embodiment, distress management program 108 further defines the trained machine learning subsystem as the function "predict_distress(sequence_of_actions)", which returns the output "final_distress_level" value, which is the level of distress predicted when the function is given a sequence of n actions as input in the created examples, such that the function predicts a level of distress as a consequence of a sequence of events. In one embodiment, distress management program 108 updates the distress prediction rule over time by considering each newly created example and reconsidering previously generated examples, which facilitates greater accuracy in distress prediction. In one embodiment, distress management program 108 utilizes newly created examples to improve accuracy of the distress prediction rule by retraining the machine learning subsystem on all available examples. Utilization of the distress prediction rule is discussed in further detail in FIG. 3.

Figure 3:
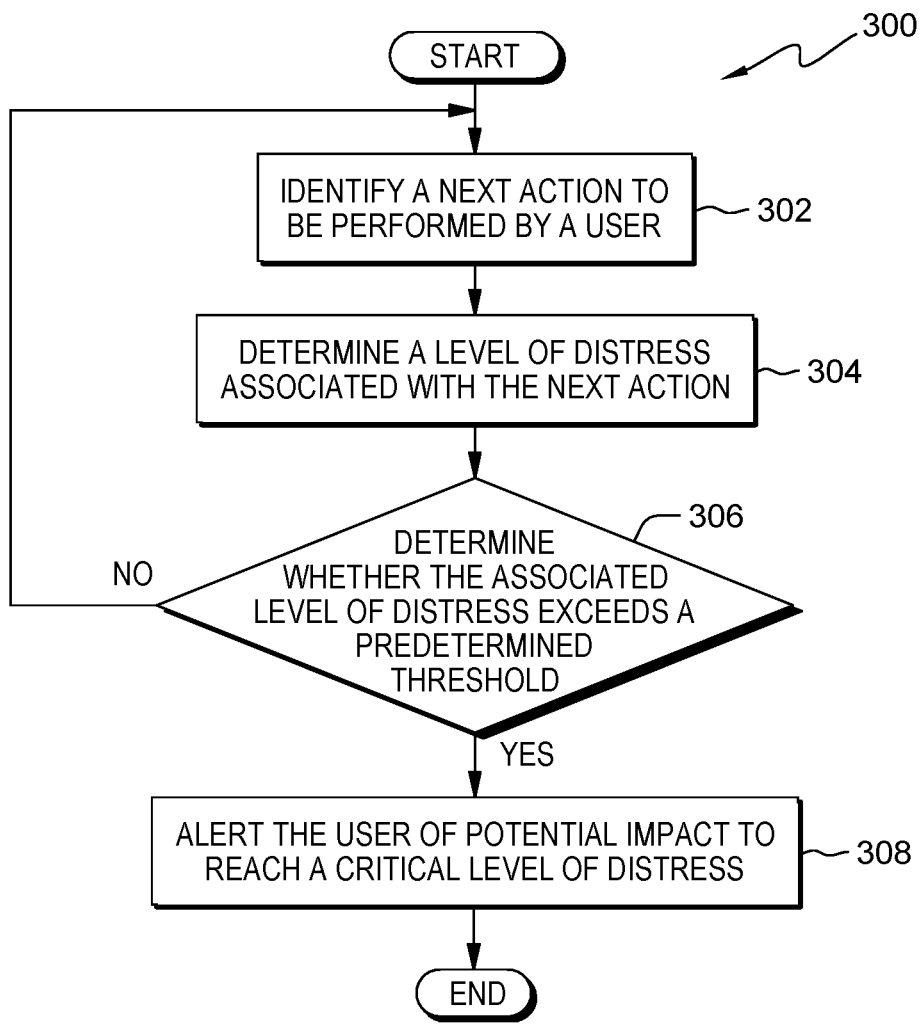
FIG. 3 is a flowchart depicting operational steps of a distress detector, in accordance with an embodiment of the present invention.

FIG. 3 depicts a flowchart of operational steps of a distress management program, such as distress management program 108 of FIG. 1, generally designated 300, for performing a detecting phase utilizing a distress detector, such as distress detector 114 of FIG. 1, in accordance with an embodiment of the present invention.

Distress management program 108 identifies a next action to be performed by a user (302). In one embodiment, distress management program 108 identifies a next action to be performed by a user by utilizing an emulator defined as a function "guess_next_action(sequence_of_actions)", which returns an output "guessed_action", and where the "sequence_of_actions" the last n−1 (i.e., n minus 1) actions performed by the user, followed by the guessed next action. For example, distress management program 108 may utilize a function to identify a potential next action to be performed by a user, where the input to the function is a sequence of the last performed actions from one or more created examples, and where the output is a "guess" of the next action to be performed by the user.

In an alternative embodiment, distress management program 108 identifies a next action to be performed by monitoring user input data, such as user input data 118. In one embodiment, distress management program 108 collects the user input data reported by a plurality of sensors, such as mobile device 102, in real-time, where the user input data may include events and sequences of events, physiological feedback and sentiment analysis. For example, in real-time, distress management program 108 may monitor user input data for a user, and detect a sequence of events beginning with "<training in the morning, heavy traffic to work . . . >", as well as a slight increase in the user's heart rate and blood pressure. In one embodiment, distress management program 108 monitors user input data transparently, without requiring a user to continuously manually update the user input data. In one embodiment, distress management program 108 determines a next action to be performed based on likely actions to follow from a historical sequence of actions saved in a knowledgebase, such as database 112.

In an alternative embodiment, distress management program 108 identifies a next action to be performed by determining whether an event is relevant to a critical level of distress. Responsive to collecting an event or sequence of events gathered from the plurality of sensors, distress management program 108 determines whether the event or sequence of events is relevant to a critical level of distress by determining whether the event or sequence of events is similar to a historical event or historical sequence of events corresponding to the critical level of distress for a user. In one embodiment, distress management program 108 queries a knowledge base, such as database 112, that is populated with a user record and a plurality of associated entries that include the historical events or historical sequences of events that corresponded to a critical level of distress. In one embodiment, distress management program 108 determines whether an event or sequence of events is similar to a historical event or historical sequence of events corresponding to the critical level of distress by determining whether the event or sequence of events matches a historical event or historical sequence of events cataloged as an entry in a user record for the user in the knowledge base, such as database 112. For example, where a user alerted a critical level of distress was reached for a historical sequence of events <training in the morning, heavy traffic on drive home, ordered fast food>, and distress management program 108 collected an event or sequence of events that starts out <training in the morning, heavy traffic on drive home . . . >, distress management program 108 may determine the collected event or sequence of events is relevant to the critical level of distress for the user based, at least in part, on the matching of the first two events in the collected sequence and the historical sequence. Conversely, where distress management program 108 collected an event or sequence of events that starts out <reading newspaper, brunch with friends . . . >, distress management program 108 may determine the collected event or sequence of events is not relevant to the critical level of distress for the user based, at least in part, on no matching events exist between the collected sequence of events and the historical sequence of events.

In another alternative embodiment, distress management program 108 may determine whether the event or sequence of events is relevant to the critical level of distress by utilizing a time distribution threshold, where the time distribution threshold is an interval of time (i.e., time spacing or time elapsed) derived from a timing of occurrence between each discrete historical event in a historical sequence of events that resulted in escalation of a cumulative level of distress to a critical level of distress for a user. In one embodiment, distress management program 108 may determine whether an event or sequence of events is relevant by comparing the time distribution threshold for matched historical events or historical sequences of events against a timing interval associated with the collected event or sequence of events to determine similarity based on the timing intervals between event occurrences. In one embodiment, distress management program 108 may determine an event or sequence of events is relevant to a critical level of distress where a timing interval for the collected event or sequence of events is less than or equal to the time distribution threshold for the matched historical events or sequence of historical events. For example, distress management program 108 may set a time distribution threshold as one or more hours, one or more days, or one or more weeks between an occurrence of sequential historical events that correspond to a critical level of distress for a user, and where a time interval between the collected events is less than or equal to the time distribution threshold, distress management program 108 may determine a high relevancy for the collected event or sequence of events (i.e., the collected event or sequence of events is likely to elevate a level of distress to a critical level for the user). Conversely, where a time interval between the collected events is greater than the time distribution threshold, distress management program 108 may determine that the event or sequence of events is not relevant, as the increased spacing of time between occurrences would lower an impact on the critical level of distress.

Distress management program 108 determines a level of distress associated with the next action (304). In one embodiment, distress management program 108 predicts a level of distress likely to be produced with performance of the next action, in light of the previous n–1 events that occurred. In one embodiment, distress management program 108 determines a level of distress associated with the next action by applying a distress prediction rule to the potential next action to be performed by the user. In one embodiment, distress management program 108 applies the distress prediction rule by applying a learned function "predict_distress" to a last performed sequence of actions plus the potential next action to be performed to determine the level of distress associated with the next action. For example, distress management program 108 performs a preprocessing function, where the preprocessing function includes generating a hypothetical scenario, where the hypothetical scenario considers the last performed actions in the current sequence of events, and the associated level of distress, then adding the potential next action to be performed at end of the last performed sequence of events to create a second hypothetical sequence of events. Next, distress management program 108 performs the processing function for determining the level of distress associated with the next action by applying a distress prediction rule to the second hypothetical sequence of events (i.e., the new hypothetical sequence of actions), where the output of the function is a level of distress associated with the second hypothetical sequence of events, and highlights the impact of the potential next action to be performed on the level of distress.

Distress management program 108 determines whether the associated level of distress exceeds a predetermined threshold (306). In one embodiment, distress management program 108 determines whether the associated level of distress for the next action exceeds a predetermined threshold for a cumulative level of distress for a user by comparing the level of distress associated with the last performed event, or sequence of events, to the level of distress associated with the second hypothetical sequence of events. Where the level of distress associated with the second hypothetical sequence of events is greater than the level of distress of the last performed event, or sequence of events, distress management program 108 determines that the associated level of distress for the next action exceeds the predetermined threshold. Where the level of distress associated with the second hypothetical sequence of events is equal to or less than the level of distress of the last performed event, or sequence of events, distress management program 108 determines that the associated level of distress for the next action has not exceeded the predetermined threshold.

Responsive to a determination that the associated level of distress does not exceed the predetermined threshold (NO branch, 306), distress management program 108 continues to identify a next action to be performed by a user (302).

Responsive to a determination that the associated level of distress exceeds the predetermined threshold (YES branch, 306), distress management program 108 alerts a user of a potential to reach critical level of distress (308). In one embodiment, distress management program 108 alerts the user to avoid performing the next action, as performing the next action after the last performed event, or sequence of events, will increment the cumulative level of distress to a critical level. In one embodiment, distress management program 108 alerts a user of a potential to reach a critical level of distress by sending a message to the user, where the message may be a text message, a message on a social media platform, or a pop up alert on a user interface of a mobile device, such as user interface 116 on mobile device 102. In another embodiment, distress management program 108 may alert a user of a potential to reach a critical level of distress utilizing haptic feedback through a mobile device, such as mobile device 102, and any paired or connected devices, such as a paired smartwatch.

In an alternative embodiment, responsive to a determination that the associated level of distress does not exceed the predetermined threshold, distress management program 108 may alert a user that performing the next action may improve a cumulative level of distress by reducing or avoiding a negative change to the level of distress.

In an alternative embodiment, distress management program 108 may provide a recommendation based, at least in part, on a knowledge base, such as database 112, of one or more events to undertake to lower a level of distress for the user and avoid escalation to a critical level of distress.

In an alternative embodiment, responsive to a determination that the associated level of distress exceeds the predetermined threshold, distress management program 108 may determine whether there are additional potential next actions to examine for impact on the cumulative level of distress. In one embodiment, distress management program 108 may determine there are additional potential next actions to examine for impact on the cumulative level of distress where similar alternative potential next actions may be performed by the user, or where the user indicates a particular next action to be performed. In one embodiment, responsive to a determination that additional potential next actions are to be examined for impact on the cumulative level of distress of a user, distress management program 108 continues to identify next actions to be performed by the user.

Figure 4:
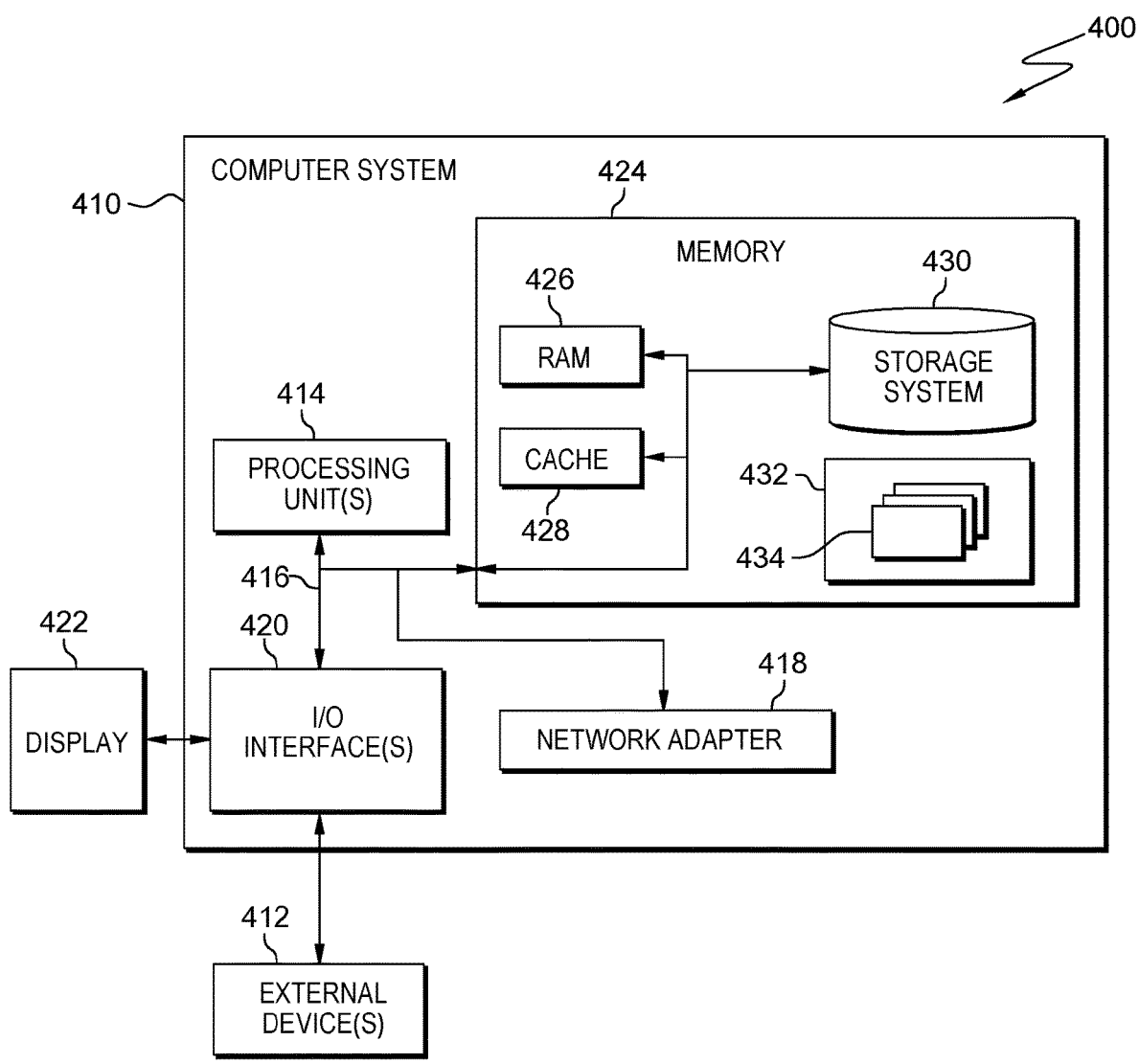
FIG. 4 is a block diagram depicting components of a data processing system (e.g., server computer of FIG. 1), in accordance with an embodiment of the present invention.

FIG. 4 depicts a block diagram of components of data processing system, such as server computer 104 of FIG. 1, generally designated 400, in accordance with an illustrative embodiment of the present invention. It should be appreciated that FIG. 4 provides only an illustration of one implementation and does not imply any limitations with regard to the environments in that different embodiments may be implemented. Many modifications to the depicted environment may be made.

In the illustrative embodiment, server computer 104 in distributed data processing environment 100 is shown in the form of a general-purpose computing device, such as computer system 410. The components of computer system 410 may include, but are not limited to, one or more processors or processing unit(s) 414, memory 424 and bus 416 that couples various system components including memory 424 to processing unit(s) 414.

Bus 416 represents one or more of any of several types of bus structures, including a memory bus or memory controller, a peripheral bus, an accelerated graphics port and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus and Peripheral Component Interconnect (PCI) bus.

Computer system 410 typically includes a variety of computer system readable media. Such media may be any available media that is accessible by computer system 410 and it includes both volatile and non-volatile media, removable and non-removable media.

Memory 424 can include computer system readable media in the form of volatile memory, such as random access memory (RAM) 426 and/or cache memory 428. Computer system 410 may further include other removable/non-removable, volatile/non-volatile computer system storage media. By way of example only, storage system 430 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk") and an optical disk drive for reading from or writing to a removable, non-volatile optical disk, such as a CD-ROM, DVD-ROM or other optical media can be provided. In such instances, each can be connected to bus 416 by one or more data media interfaces. As will be further depicted and described below, memory 424 may include at least one computer program product having a set (e.g., at least one) of program modules that are configured to carry out the functions of embodiments of the invention.

Program/utility 432, having one or more sets of program modules 434, may be stored in memory 424 by way of example and not limitation, as well as an operating system, one or more application programs, other program modules and program data. Each of the operating systems, one or more application programs, other program modules and program data or some combination thereof, may include an implementation of a networking environment. Program modules 434 generally carry out the functions and/or methodologies of embodiments of the invention as described herein. Computer system 410 may also communicate with one or more external device(s) 412, such as a keyboard, a pointing device, a display 422, etc. or one or more devices that enable a user to interact with computer system 410 and any devices (e.g., network card, modem, etc.) that enable computer system 410 to communicate with one or more other computing devices. Such communication can occur via Input/Output (I/O) interface(s) 420. Still yet, computer system 410 can communicate with one or more networks, such as a local area network (LAN), a general wide area network (WAN) and/or a public network (e.g., the Internet) via network adapter 418. As depicted, network adapter 418 communicates with the other components of computer system 410 via bus 416. It should be understood that although not shown, other hardware and software components, such as microcode, device drivers, redundant processing units, external disk drive arrays, RAID systems, tape drives and data archival storage systems may be used in conjunction with computer system 310.

The present invention may be a system, a method and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable) or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems) and computer program products according to embodiments of the invention. It will be understood that each block of the flowchart illustrations and/or block diagrams and combinations of blocks in the flowchart illustrations and/or block diagrams, can be implemented by computer readable program instructions.

These computer readable program instructions may be provided to a processor of a general purpose computer, a special purpose computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus or other device to cause a series of operational steps to be performed on the computer, other programmable apparatus or other device to produce a computer implemented process, such that the instructions which execute on the computer, other programmable apparatus or other device implement the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace or to enable others of ordinary skill in the art to understand the embodiments disclosed herein.

The terminology used herein is for the purpose of describing particular embodiments only and is not intended to be limiting of the invention. It should be appreciated that any particular nomenclature herein is used merely for convenience and thus, the invention should not be limited to use solely in any specific function identified and/or implied by such nomenclature. Furthermore, as used herein, the singular forms of "a", "an", and "the" are intended to include the plural forms as well, unless the context clearly indicates otherwise.

What is claimed is:

1. A method comprising:
    determining, by one or more computer processors, a level of distress associated with a user;
    identifying, by the one or more computer processors, a next action to be performed by the user;
    determining, by the one or more computer processors, a level of distress associated with the next action;
    determining, by the one or more computer processors, whether the level of distress associated with the next action exceeds a predetermined threshold; and
    responsive to a determination that the level of distress associated with the next action exceeds the predetermined threshold, alerting, by the one or more computer processors, the user of an impact to the level of distress associated with the user.

2. The method of claim 1, wherein determining a level of distress associated with a user further comprises:
    collecting, by the one or more computer processors, user input data through one or more sensors, wherein the one or more sensors are capable of providing sensor values related to physiological quantities associated with the user, communication activities related to the user, location data related to the user and data manually entered by the user.

3. The method of claim 1, further comprising:
    creating, by the one or more computer processors, an event corresponding to the level of distress associated with the user and a current action performed by the user;
    creating, by the one or more computer processors, an example of a sequence of events that correspond to a critical level of distress for a user, wherein creating the example includes determining whether a threshold number of events were created by comparing a number of created events to a predetermined threshold number of events estimated to return workable results for training a rule to predict_distress; and
    generating, by the one or more computer processors, a distress prediction rule utilizing a first function that receives as input one or more created examples to return a second function, wherein the second function outputs distress predictions based on an input of one or more events.

4. The method of claim 1, wherein identifying a next action to be performed by the user further comprises at least one of:
    performing, by the one or more computer processors, a function to identify the next action to be performed by the user, where an input to the function is a sequence of the last performed actions from one or more created examples, and where an output is a guess of the next action to be performed by the user;
    determining, by the one or more computer processors, a potential next action to be performed based on likely actions to follow from a historical sequence_of_actions saved in a knowledgebase, wherein determining the potential next action includes monitoring user input data transparently to detect the historical sequence_of_actions; and
    determining, by the one or more computer processors, whether a sequence_of_actions is similar to a historical sequence_of_actions corresponding to a critical level of distress for the user.

5. The method of claim 1, wherein determining a level of distress associated with the next action further comprises:
    generating, by the one or more computer processors, a hypothetical scenario, wherein the hypothetical scenario includes a last performed action in a current sequence_of_actions and an associated level of distress for the current sequence_of_actions;
    creating, by the one or more computer processors, a second hypothetical scenario, wherein the second hypothetical scenario includes a potential next action to be performed at end of a last performed sequence_of_actions; and
    applying, by the one or more computer processors, a distress prediction rule to the second hypothetical scenario, where an output of the distress prediction rule is a level of distress associated with the second hypothetical scenario indicating an impact of the potential next action on the level of distress associated with the user.

6. The method of claim 1, wherein determining whether the level of distress associated with the next action exceeds a predetermined threshold further comprises:
    determining, by the one or more computer processors, the associated level of distress for the next action exceeds the predetermined threshold where a level of distress associated with a second hypothetical sequence of events is greater than a level of distress of a last performed sequence of events.

7. The method of claim 1, wherein alerting the user of an impact to the level of distress associated with the user further comprises at least one of:
    sending, by the one or more computer processors, a message to the user to avoid performing the next action;
    alerting, by the one or more computer processors, the user of a potential to reach a critical level of distress utilizing haptic feedback through a mobile device; and
    providing, by the one or more computer processors, a recommendation of one or more actions to perform to lower the level of distress associated with the user.

8. A computer program product comprising:
    one or more computer readable storage media and program instructions stored on the one or more computer readable storage media, the program instructions comprising:
    program instructions to determine a level of distress associated with a user;
    program instructions to identify a next action to be performed by the user;
    program instructions to determine a level of distress associated with the next action;
    program instructions to determine whether the level of distress associated with the next action exceeds a predetermined threshold; and responsive to a determination that the level of distress associated with the next action exceeds the predetermined threshold, program instructions to alert the user of an impact to the level of distress associated with the user.

9. The computer program product of claim 8, wherein program instructions to determine a level of distress associated with a user further comprises:
program instructions to collect user input data through one or more sensors, wherein the one or more sensors are capable of providing sensor values related to physiological quantities associated with the user, communication activities related to the user, location data related to the user and data manually entered by the user.

10. The computer program product of claim 8, further comprising:
program instructions to create an event corresponding to the level of distress associated with the user and a current action performed by the user;
program instructions to create an example of a sequence of events that correspond to the critical level of distress for a user, wherein creating the example includes determining whether a threshold number of events were created by comparing a number of created events to a predetermined threshold number of events estimated to return workable results for training a rule to predict_distress; and
program instructions to generate a distress prediction rule utilizing a first function that receives as input one or more created examples to return a second function, wherein the second function outputs distress predictions based on an input of one or more events.

11. The computer program product of claim 8, wherein program instructions to identify a next action to be performed by the user further comprises at least one of:
program instructions to perform a function to identify the next action to be performed by the user, where an input to the function is a sequence of the last performed actions from one or more created examples, and where an output is a guess of the next action to be performed by the user;
program instructions to determine a potential next action to be performed based on likely actions to follow from a historical sequence_of_actions saved in a knowledgebase, wherein determining the potential next action includes monitoring user input data transparently to detect the historical sequence_of_actions; and
program instructions to determine whether a sequence_of_actions is similar to a historical sequence_of_actions corresponding to a critical level of distress for the user.

12. The computer program product of claim 8, wherein program instructions to determine a level of distress associated with the next action further comprises:
program instructions to generate a hypothetical scenario, wherein the hypothetical scenario includes a last performed action in a current sequence_of_actions and an associated level of distress for the current sequence_of_actions;
program instructions to create a second hypothetical scenario, wherein the second hypothetical scenario includes a potential next action to be performed at end of a last performed sequence_of_actions; and
program instructions to apply a distress prediction rule to the second hypothetical scenario, where an output of the distress prediction rule is a level of distress associated with the second hypothetical scenario indicating an impact of the potential next action on the level of distress associated with the user.

13. The computer program product of claim 8, wherein program instructions to determine whether the level of distress associated with the next action exceeds a predetermined threshold further comprises:
program instructions to determine the associated level of distress for the next action exceeds the predetermined threshold where a level of distress associated with a second hypothetical sequence of events is greater than a level of distress of a last performed sequence of events.

14. The computer program product of claim 8, wherein program instructions to alert the user of an impact to the level of distress associated with the user further comprises at least one of:
program instructions to send a message to the user to avoid performing the next action;
program instructions to alert the user of a potential to reach a critical level of distress utilizing haptic feedback through a mobile device; and
program instructions to provide a recommendation of one or more events to perform to lower the level of distress associated with the user.

15. A computer system comprising:
one or more computer processors;
one or more computer readable storage media; and
program instructions stored on at least one of the one or more computer readable storage media for execution by at least one of the one or more computer processors, the program instructions comprising:
program instructions to determine a level of distress associated with a user;
program instructions to identify a next action to be performed by the user;
program instructions to determine a level of distress associated with the next action;
program instructions to determine whether the level of distress associated with the next action exceeds a predetermined threshold; and
responsive to a determination that the level of distress associated with the next action exceeds the predetermined threshold, program instructions to alert the user of an impact to the level of distress associated with the user.

16. The computer system of claim 15, wherein program instructions to determine a level of distress associated with a user further comprises:
program instructions to collect user input data through one or more sensors, wherein the one or more sensors are capable of providing sensor values related to physiological quantities associated with the user, communication activities related to the user, location data related to the user and data manually entered by the user.

17. The computer system of claim 15, further comprising:
program instructions to create an event corresponding to the level of distress associated with the user and a current action performed by the user;
program instructions to create an example of a sequence of events that correspond to a critical level of distress for a user, wherein creating the example includes determining whether a threshold number of events were created by comparing a number of created events to a predetermined threshold number of events estimated to return workable results for training a rule to predict_distress; and program instructions to generate a distress prediction rule utilizing a first function that receives as input one or more created examples to return a second function, wherein the second function outputs distress predictions based on an input of one or more events.

18. The computer system of claim 15, wherein program instructions to identify a next action to be performed by the user further comprises at least one of:

program instructions to perform a function to identify the next action to be performed by the user, where an input to the function is a sequence of a last performed action from one or more created examples, and where an output is a guess of the next action to be performed by the user;

program instructions to determine a potential next action to be performed based on likely actions to follow from a historical sequence_of_actions saved in a knowledgebase, wherein determining the potential next action includes monitoring user input data transparently to detect the historical sequence_of_actions; and program instructions to determine whether a sequence_of_actions is similar to a historical sequence_of_actions corresponding to a critical level of distress for the user.

19. The computer system of claim 15, wherein program instructions to determine a level of distress associated with the next action further comprises:

program instructions to generate a hypothetical scenario, wherein the hypothetical scenario includes a last performed action in a current sequence_of_actions and an associated level of distress for the current sequence_of_actions;

program instructions to create a second hypothetical scenario, wherein the second hypothetical scenario includes a potential next action to be performed at end of a last performed sequence_of_actions; and program instructions to apply a distress prediction rule to the second hypothetical scenario, where an output of the distress prediction rule is a level of distress associated with the second hypothetical scenario indicating an impact of the potential next action on the level of distress associated with the user.

20. The computer system of claim 15, wherein program instructions to determine whether the level of distress associated with the next action exceeds a predetermined threshold further comprises:

program instructions to determine the associated level of distress for the next action exceeds the predetermined threshold where a level of distress associated with a second hypothetical sequence of events is greater than a level of distress of a last performed sequence of events.

* * * * *